United States Patent [19]
Wellbrock

[11] 4,279,837
[45] Jul. 21, 1981

[54] PROCESS FOR THE PREPARATION OF ALKALINE EARTH METAL SALTS OF ALKYL BENZENESULFONIC ACIDS

[75] Inventor: Werner Wellbrock, Bad Soden am Taunus, Fed. Rep. of Germany

[73] Assignee: Hoechst Aktiengesellschaft, Fed. Rep. of Germany

[21] Appl. No.: 125,462

[22] Filed: Feb. 28, 1980

[30] Foreign Application Priority Data

Mar. 2, 1979 [DE] Fed. Rep. of Germany ....... 2908265

[51] Int. Cl.³ .......................................... C07C 143/24
[52] U.S. Cl. ............................................... 260/505 N
[58] Field of Search .................................... 260/505 N

[56] References Cited

U.S. PATENT DOCUMENTS

4,129,589  12/1978  Eliades et al. ................... 260/505 N

*Primary Examiner*—Alan Siegel
*Attorney, Agent, or Firm*—Connolly and Hutz

[57] ABSTRACT

Process for the preparation of alkaline earth metal salts of alkyl benzene sulfonic acids by the neutralization of alkyl benzenesulfonic acids, which comprises neutralizing the alkyl benzene sulfonic acid with the necessary amount of a basic alkaline earth metal compound in an inert organic solvent and in the presence of 1 to 10% by weight of an oxalkylate, calculated on the weight of the alkyl benzene sulfonic acid.

2 Claims, No Drawings

PROCESS FOR THE PREPARATION OF ALKALINE EARTH METAL SALTS OF ALKYL BENZENESULFONIC ACIDS

Alkaline earth metal salts of alkyl benzenesulfonic acids are widely used on an industrial scale for the preparation of emulsion concentrates of water-insoluble biocides, especially for insecticides and herbicides. The products used for this purpose must be essentially anhydrous. These compounds are prepared in known manner according to a two-step process. Starting from alkyl benzenesulfonic acid which is obtained according to common sulfonation processes from alkyl benzenes of from about 9 to 18 carbon atoms in the alkyl radicals, the desired alkaline earth metal salt, above all the calcium salt, is at first prepared in an aqueous medium. Since the attempts to effect the neutralization of alkyl benzenesulfonic acids with alkaline earth metal hydroxide, especially with calcium or barium hydroxide, in the absence of water have not been successful so far, said neutralization is executed in an aqueous organic solvent, generally in aqueous lower alcohols, especially isobutanol. Thereafter the water and a large proportion of the organic solvent are removed by azeotropic distillation from the resulting neutral solution of the alkyl benzenesulfonates in the aqueous solvent.

It has now been found that the addition of water is superfluous if the neutralization is carried out in the presence of small amounts of an oxalkylate.

Thus the subject of the invention is a process for the preparation of alkaline earth metal salts, especially calcium salts, of alkyl benzenesulfonic acids by neutralizing the corresponding free alkyl benzenesulfonic acids, which comprises adding from 1 to 10, preferably from 1 to 5% by weight of an oxalkylate, calculated on the weight of the alkyl benzenesulfonic acid, to a solution of the alkyl benzenesulfonic acid in an organic solvent, neutralizing the same by adding the necessary amount of a basic alkaline earth metal compound and isolating the resulting salt of the alkyl benzenesulfonic acid.

The process of the invention is generally carried out by introducing the solvent into a reaction vessel, adding the neutralizing agent and the oxalkylate, heating the mixture to a temperature of from about 70° to 90° C., and then adding the alkyl benzenesulfonic acid. Upon completion of the neutralization, which may be determined by checking the pH value, the alkyl benzenesulfonate formed is isolated by filtration. The individual products my also be added to the organic solvent in a modified order, however, the above-described mode of operation being preferred.

In order to remove the reaction water being formed in the neutralization process, said water is extracted, together with part of the solvent, by azeotropic distillation upon completion of the neutralization. This distillation process may be carried out before ar after the filtration, depending on whether the alkyl benzene sulfonate is to be obtained in a solid form or as an anhydrous formulation in the organic solvent.

Suitable solvents for this process are lower alcohols, especially i-butanol and i-propanol, but also aromatic solvents, such as p-xylene, benzene, toluene and mineral oils. The alkyl benzenesulfonic acids concerned are the monosulfonic acids of alkyl benzenes having from 8 to 18 carbon atoms in the alkyl radicals. As oxalkylates, there may be used products of the following classes of compounds:

Oxethylated triglycerides having from 20 to 60 units of ethylene oxide, preferably castor oil having from 36 to 40 ethylene oxide units; oxalkylated $C_{12}$–$C_{20}$ fatty alcohols or fatty acids having from 4 to 30 ethylene oxide units each; oxalkylated alkyl phenols of from 8 to 18 carbon atoms in the alkyl chains and having 8 to 30 ethylene oxide units as well as polyethylene-glycol methyl- or -ethyl ethers of from 1 to 8 ethylene glycol units. As neutralizing agents there may be used basic compounds of the alkaline earth metals, preferably calcium hydroxide, calcium carbonate or calcium oxide.

The above-described process offers the advantage that the addition of water may be dispensed within the neutralization process, which helps to save time and energy.

The following Examples illustrate the invention.

EXAMPLE 1

813 Milliliters of xylene are introduced into a reaction vessel and 30 g of $Ca(OH)_2$ are added, while stirring. Stirring is continued for 10 minutes, then 16 g of diehtylene-glycol dimethyl ether are added, and the mixture is heated to 70° C. Within 3 hours, 250 g of dodecyl benzenesulfonic acid are added, until a pH of 4 has been reached. Stirring is continued for another 30 minutes, and the mixture is further heated up to an internal temperature of 142° C. In the course of this process about 200 ml of a xylene-water mixture are removed by distillation. The vessel contents are cooled to 70° C., continued to be stirred for 30 minutes and filtered off. There are obtained about 800 g of the calcium salt of dodecyl benzenesulfonic acid.

EXAMPLE 2

3 Grams of an oxalkylated nonylphenol with 9 units of ethylene oxide are added to 100 g of anhydrous i-butanol, and 13.5 g of $Ca(OH)_2$ are added to the resulting mixture. It is then heated to 70° C., and 93 g of dodecyl benzenesulfonic acid are slowly added, while stirring, until a pH of about 6 has been reached. Stirring is continued for one hour, and the calcium salt is filtered off.

The water having been formed in the neutralization process is removed by azeotropic distillation. In this operation, about 72 ml of i-butanol are removed altogether which contain the entire amount of water. There are obtained 140 g of anhydrous calcium-dodecyl benzenesulfonate of 70% strength.

What is claimed is:

1. Process for the preparation of alkaline earth metal salts of alkyl benzene sulfonic acids by the neutralization of alkyl benzenesulfonic acids, which comprises neutralizing the alkyl benzene sulfonic acid with the necessary amount of a basic alkaline earth metal compound in an inert organic solvent and in the presence of 1 to 10% by weight of an oxalkylate, calculated on the weight of the alkyl benzene sulfonic acid.

2. A process as claimed in claim 1 which comprises adding first the oxalkylate and the basic alkaline earth metal compound to the inert solvent and then adding the alkyl benzene sulfonic acid.

* * * * *